United States Patent
Weber et al.

(10) Patent No.: US 8,114,633 B2
(45) Date of Patent: Feb. 14, 2012

(54) METHODS FOR DIFFERENTIATING PLASMA-DERIVED PROTEIN FROM RECOMBINANT PROTEIN IN A SAMPLE

(75) Inventors: Alfred Weber, Vienna (AT); Peter Turecek, Kosterneuburg (AT); Hans-Peter Schwarz, Vienna (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 408 days.

(21) Appl. No.: 12/341,098

(22) Filed: Dec. 22, 2008

(65) Prior Publication Data

US 2009/0221100 A1 Sep. 3, 2009

Related U.S. Application Data

(60) Provisional application No. 61/017,091, filed on Dec. 27, 2007.

(51) Int. Cl.
*C12P 21/04* (2006.01)
*C12P 21/08* (2006.01)
*G01N 31/00* (2006.01)
*G01N 33/86* (2006.01)

(52) U.S. Cl. ......... 435/69.7; 435/7.1; 435/13; 435/69.6; 436/8; 436/15; 436/16; 436/69; 436/827; 530/380; 530/383; 530/387.3; 530/387.5; 530/395; 530/396

(58) Field of Classification Search ............ 435/7.1, 435/13, 69.6, 69.7, 358; 436/16, 69, 827, 436/8, 15; 530/380, 383, 384, 387.3, 387.5, 530/388.25, 395, 396

See application file for complete search history.

(56) References Cited

U.S. PATENT DOCUMENTS

| | | | |
|---|---|---|---|
| 4,391,904 A | 7/1983 | Litman et al. | |
| 5,047,335 A | 9/1991 | Paulson et al. | |
| 5,225,542 A | 7/1993 | Cramer et al. | |
| 5,395,924 A * | 3/1995 | Blattler et al. | 530/396 |
| 5,994,129 A | 11/1999 | Armstrong et al. | |
| 6,048,729 A | 4/2000 | Selden et al. | |
| 6,063,630 A | 5/2000 | Treco et al. | |
| 7,838,634 B2 * | 11/2010 | Haab et al. | 530/387.1 |
| 2006/0160948 A1 | 7/2006 | Scheiflinger et al. | |

FOREIGN PATENT DOCUMENTS

WO WO-99/64072 12/1999
WO WO-2006/113245 10/2006

OTHER PUBLICATIONS

Bragonzi et al. A new Chinese hamster ovary cell line expressing α2,6-sialyltransferase used as universal host for the production of human-like sialylated recombinant glycoproteins, Biochimica et Biophysica Acta 1474: 273-282 (2002).*

Altmann et al. Insect cells as hosts for the expression of recombinant glycoprotein, Glycoconjugate Journal 16: 109-123 (1999).*

(Continued)

*Primary Examiner* — Gail R Gabel
(74) *Attorney, Agent, or Firm* — Marshall, Gerstein & Borun LLP (57) ABSTRACT

The present invention relates, in general, to methods for detecting and quantitating plasma-derived protein and recombinant protein in a sample based on the difference in protein glycosylation, when the plasma protein and the recombinant protein are essentially the same protein.

17 Claims, 2 Drawing Sheets

OTHER PUBLICATIONS

Fischer et al. Sialic acid-binding lectins: submolecular specificity and interaction with sialoglycoproteins and tumour cells, Glycoconjugate Journal, 12:707-713 (1995).*

Altmann et al., "Insect cells as hosts for the expression of recombinant glycoproteins", *Glycoconj. J.*, 16:109-23 (1999).

Ao et al., "Fluoroimmunoassay for antigen based on fluorescence quenching signal of gold nanoparticles", *Anal. Chem.*, 78:1104-6 (2006).

Aumiller et al., "A transgenic insect cell line engineered to produce CMP-sialic acid and sialylated glycoproteins", *Glycobiology*, 13:497-507 (2003).

Bragonzi et al., "A new Chinese hamster ovary cell line expressing alpha2,6-sialyltransferase used as universal host for the production of human-like sialylated recombinant glycoproteins", *Biochim. Biophys. Acta*, 1474:273-82 (2000).

Brinkman-Van Der Linden et al., "Effects of sialic acid substitutions on recognition by Sambucus nigra agglutinin and Maackia amurensis hemagglutinin", *Anal. Biochem.*, 303:98-104 (2002).

Brooks, "Protein glycosylation in diverse cell systems: implications for modification and analysis of recombinant proteins", *Expert Rev. Proteomics*, 3:345-59 (2006).

Chen et al., "A gold nanoparticles/sol-gel composite architecture for encapsulation of immunoconjugate for reagentless electrochemical immunoassay", *Biomaterials*, 27:2313-21 (2006).

Chenu et al., "Reduction of CMP-N-acetylneuraminic acid hydroxylase activity in engineered Chinese hamster ovary cells using an antisense-RNA strategy", *Biochim. Biophys. Acta*, 1622:133-44 (2003).

Coelho et al., "Magnetic polysiloxane-polyvinyl alcohol composite as solid-phase in chemiluminescent assays", *Biotechnology Letters*, 24:1705-8 (2002).

Coligan et al., "Commonly used detergents", *Current Protocols in Protein Science*, Appendix 1B, A.1B.1-A.1B.3 (1998).

Cui et al., "Synthesis of AgcoreAushell bimetallic nanoparticles for immunoassay based on surface-enhanced Raman spectroscopy", *J. Phys. Chem. B*, 110:4002-6 (2006).

Dai et al., "Electrochemical sensor for immunoassay of carcinoembryonic antigen based on thionine monolayer modified gold electrode", *Cancer Detect Prev.*, 29:233-40 (2005).

Debray et al., "Specificity of twelve lectins towards oligosaccharides and glycopeptides related to N-glycosylproteins", *Eur. J. Biochem.*, 117:41-55 (1981).

Ebinuma et al., "A novel ELISA system for selective measurement of human adiponectin multimers by using proteases," *Clin. Chimica Acta*, 372:47-53 (2006).

Ferrand et al., "A synthetic lectin analog for biomimetic disaccharide recognition", *Science*, 318:619-22 (2007).

Fischer et al., "Sialic acid-binding lectins: submolecular specificity and interaction with sialoglycoproteins and tumour cells", *Glycoconj. J.*, 12:707-13 (1995).

Gerngross, "Advances in the production of human therapeutic proteins in yeasts and filamentous fungi", *Nat. Biotechnol.*, 22:1409-14 (2004).

Ghindilis, "Direct electron transfer catalysed by enzymes: application for biosensor development", *Biochem. Soc. Trans.*, 28:84-9 (2000).

Gruppo et al., "Comparative effectiveness of full-length and B-domain deleted factor VIII for prophylaxis—a meta-analysis", *Haemophilia*, 9:251-60 (2003).

Hale-Donze et al., "Measurement of TGF-β in biological fluids", *Current Protocols in Immunology*, 6.11.1-6.11.21 (2001).

International Search Report and Written Opinion for corresponding International Application No. PCT/US08/087934 (Apr. 24, 2009).

Liu et al., "Solid-substrate room-temperature phosphorescence immunoassay based on an antibody labeled with nanoparticles containing dibromofluorescein luminescent molecules and analytical application", *J. Immunol. Methods*, 307:34-40 (2005).

Paccalet et al., "Engineering of a sialic acid synthesis pathway in transgenic plants by expression of bacterial Neu5Ac-synthesizing enzymes", *Plant Biotechnol. J.*, 5:16-25 (2007).

Pitas et al., "Anti-phencyclidine monoclonal antibody binding capacity is not the only determinant of effectiveness, disproving the concept that antibody capacity is easily surmounted", *Drug Metab. Dispos.*, 34:906-12 (2006).

Saenko et al., "Strategies towards a longer acting factor VIII", *Haemophilia*, 12 Suppl 3: 42-51 (2006).

Saint-Jore-Dupas et al., "From planta to pharma with glycosylation in the toolbox", *Trends Biotechnol.*, 25:317-23 (2007).

Schultz et al., "Single-target molecule detection with nonbleaching multicolor optical immunolabels", *Proc. Natl. Acad. Sci. USA*, 97:996-1001 (2000).

Sun et al., "Single-event analysis of the packaging of bacteriophage T7 DNA concatemers in vitro", *Biophys. J.*, 77:1627-37 (1999).

Tomiya et al., "Comparing N-glycan processing in mammalian cell lines to native and engineered lepidopteran insect cell lines", *Glycoconj. J.*, 21:343-60 (2004).

Vajo et al., "Genetically engineered insulin analogs: diabetes in the new millenium", *Pharmacol. Rev.*, 52:1-9 (2000).

Weber et al., "Selective measurement of human recombinant von Willebrand Factor (rVWF)," Congress Program, Poster Session, 53rd Annual Meeting—Society of Thrombosis and Haemostasis Research (Jan. 2009).

Werner et al., "Glycosylation of therapeutic proteins in different production systems", *Acta Paediatr. Suppl.*, 96:17-22 (2007).

Wildt et al., "The humanization of N-glycosylation pathways in yeast", *Nat. Rev. Microbiol.*, 3:119-28 (2005).

Zhao et al., "Comparative serum glycoproteomics using lectin selected sialic acid glycoproteins with mass spectrometric analysis: application to pancreatic cancer serum," *J. Proteome Res.*, 5:1792-802 (2006).

Zhou et al., "Two-color, rolling-circle amplification on antibody microarrays for sensitive, multiplexed serum-protein measurements," *Genome Biology*, 5:R28 (2004).

Gabius et al. (eds.), *Glycosciences: Status and Perspectives*, Table of Contents, Chapter 10—Lectins as Tools for Glycoconjugate Purificiation and Characterization, Weinheim: Chapman & Hall (1997), Table of Contents only.

Jenkins et al., "Getting the glycosylation right: implications for the biotechnology industry", *Nat. Biotechnol.*, 14:975-81 (1996).

Physicians Desk Reference, 62nd ed., Table of Contents, Section 5, product information, Montvale, NJ: Thomas Healthcare (2008), Table of Contents only.

* cited by examiner

METHODS FOR DIFFERENTIATING PLASMA-DERIVED PROTEIN FROM RECOMBINANT PROTEIN IN A SAMPLE

This application claims the priority benefit of U.S. Provisional Application No. 61/017,091, filed Dec. 27, 2007, herein incorporated by reference in its entirety.

FIELD OF THE INVENTION

The invention relates, in general, to methods to differentiate and quantitate plasma derived protein and recombinant protein in a sample using a glycosylation-specific binding assay.

BACKGROUND OF THE INVENTION

Glycosylation is the process of, or the result of, addition of carbohydrates (saccharides) to proteins and lipids. The glycosylation process is a co-translational and post-translational modification that takes place during the synthesis of membrane and secreted proteins. The majority of proteins synthesized in the rough endoplasmic reticulum (ER) undergo glycosylation (Brooks et al., Expert Rev Proteomics 3:345-59, 2006). Glycosylation is an enzyme-directed, site-specific process, having two specific types of attachment, N-linked glycosylation and O-linked glycosylation. N-linked carbohydrates are attached via N-acetylglucosamine linked to the amino acid asparagine at an amino acid consensus sequence "Asn-X-Ser/Thr." The surrounding amino acids often dictate what type of, if any, glycosylation will take place. For example, if the middle amino acid in the consensus sequence is proline (Pro), no N-linked glycosylation takes place. Most O-linked carbohydrate covalent attachments to proteins involve a linkage between the monosaccharide N-acetylgalactosamine and the amino acids serine or threonine (Werner et al., Acta Pediatrica 96:17-22, 2007). There is no consensus sequence for O-linked glycosylation.

Glycosylation on protein may result in either addition of simple sugar residues such as mannose and glucose, or addition of more complex sugar residues such as sialic acid and fucose (Brooks et al., Expert Rev Proteomics 3:345-59, 2006), and branched chain sugars. Protein glycosylation serves several functions in vivo, including stabilization of the protein in the cytoplasm, increasing protein half-life, as well as regulating the activity of the protein or enzyme having the glycosyl residues (Werner et al., Acta Pediatrica 96:17-22, 2007). Thus, it is important to ensure that proteins express the correct glycosylation or the protein activity may be compromised or absent. The type of glycosylation on a protein often depends on the cell type in which the protein is synthesized, as well as the species of cell synthesizing the protein (Werner et al., supra; Brooks et al., supra). For example, bacteria and yeast do not synthesize complex glycans which are typically found on higher eukaryotic proteins (Brooks et al., supra). Even within mammalian species (e.g., human and hamster), and from tumor cells to normal, non-malignant cells, glycosylation patterns can be different (Werner et al., supra). Thus, the type of cell system in which the protein is produced has a significant influence on the resulting glycosylated product (Werner et al., supra).

Recombinantly produced proteins have provided a significant improvement to the study of proteins in both clinical and research settings. The large scale production of recombinant proteins has enabled the study of protein activity in vitro, and recombinant proteins have recently been used as therapeutic agents in the clinical setting. For example, recombinant interleukin-2 has been administered to cancer patients to boost the immune system after chemotherapy, and recombinant growth factors, such as human growth hormone, erythropoietin and granulocyte colony stimulating factor, and blood factors, such as Factor VIII and Factor VII, are used in the treatment of various disorders.

Although recombinant proteins provide an advantage as therapeutic proteins, they also exhibit certain drawbacks. It can be difficult to produce sufficient amounts of recombinant protein for therapeutic use in human cells in a cost efficient manner, and recombinant protein made in such cells as *Escherichia coli* and other bacteria do not necessarily fold properly, are not glycosylated, and/or must be manipulated once isolated to manufacture proteins in a form active in the human body. Additionally, glycosylation of proteins in human cells is often more complex than that seen in commonly used protein expression systems, such as bacteria, insects and even higher mammals. For example, insect cells such as *Spodoptera* rarely generate proteins having higher order sugar structure of the types produced in mammals (Altmann et al., Glycoconjugate J 16:109-123, 1999). Further, although most mammals express higher order sugars comprising such structures as fucose and sialic acid residues, these sugar moieties may not be chemically attached in the same manner as the sugars in proteins produced in human cells (Jenkins et al., Nature Biotechnology 14:975-981, 1996; U.S. Pat. No. 5,047,335).

Administration of therapeutic proteins is often used in order to correct a deficiency or functional defect in the endogenously expressed protein. Recombinant insulin and insulin analogs (Vajo et al., Pharmacol Rev. 52:1-9, 2000) are administered to diabetic patients to make up for the lack of naturally produced insulin Recombinant Factor VIII and sequence analogs of Factor VIII are administered to patients suffering from hemophilia A to correct a deficiency in Factor VIII levels resulting in aberrant blood clotting (Gruppo et al., Haemophilia. 9:251-60, 2003). In recombinant therapies of these types, it is useful to determine the levels of recombinant protein in serum or other sample in order to determine the half-life of the drug and other pharmacokinetics, such as absorption, in the patient. However, it can be difficult to determine the difference between the endogenous protein and the recombinant protein, since they are essentially the same protein.

Thus, there remains a need in the art to develop methods to differentiate the amount of naturally-derived protein from the exogenous protein in a sample and to detect the levels of endogenous and exogenous recombinant protein administered to a patient in order that treatment regimens may be optimized.

SUMMARY OF THE INVENTION

The present invention relates in general to methods for differentiating the presence of plasma-derived protein in a sample from a recombinantly produced protein in the sample, when the plasma-derived protein and the recombinant protein are essentially the same protein, by exploiting the difference in glycosylation patterns between plasma proteins and recombinant proteins. The invention also provides a method to quantitate the levels of plasma-derived protein in a sample using the expression of a particular carbohydrate moiety.

In one aspect, the invention provides a method to quantitate the amount of plasma-derived protein (pdP) and recombinant protein (rP) in a sample, wherein the plasma-derived protein and recombinant protein are the same protein with different glycosylation patterns, said different glycosylation patterns giving rise to different degrees of lectin binding for the plasma-derived protein compared to the recombinant protein, wherein total protein (tP) in said sample is pre-determined and equal to the combined amounts of plasma-derived protein and recombinant protein (pdP+rP), said method comprising the steps of: (a) calculating a difference between lectin binding for said sample and expected lectin binding for a hypothetical sample of equal volume having an amount of protein equal to tP, wherein expected lectin binding is determined from a standard curve of lectin binding versus increasing amounts of recombinant protein, and, (b) plotting the difference from (a) on a calibration curve to determine the amount of recombinant protein (rP) in said sample, wherein the calibration curve is a plot of the difference between expected lectin binding, calculated as in (a), and observed lectin binding for mixtures containing known amounts of pdP and rP, as a function of increasing amounts of recombinant protein (rP) in said mixtures, said mixtures each having a constant amount of pdP.

In one embodiment, the calculating step comprises contacting the sample with a lectin composition, wherein the lectin is labeled with a detectable label. The calculating step further comprises detecting the labeled lectin composition using methods described herein in the detailed description.

In a further embodiment, the method provides that the amount of total protein is pre-determined by measuring the amount of recombinant protein and plasma-derived protein in a sample. The amount of total protein is measured using methods well-known in the art, such as, in one aspect, an enzyme linked immunosorbant assay (ELISA). In a related embodiment, the expected lectin binding of a sample is determined by assuming that the total amount of protein in the sample is all plasma-derived protein and extrapolating the amount of lectin binding expected based on that amount of plasma-derived protein.

In an additional embodiment, the method provides that the calibration curve is prepared before quantitating the amount of plasma-derived and recombinant protein in a sample. It is contemplated that the calibration curve is plotted as the difference between i) expected lectin binding of a sample containing a known total amount of recombinant and plasma-derived protein and ii) the lectin binding observed for those mixtures containing known amounts of pdP and rP, plotted as a function of increasing amounts of rP in said mixtures, said mixtures each having a constant amount of pdP.

In a related embodiment, the lectin is any lectin as described herein which demonstrates specific binding to a sugar moiety found on a human plasma-derived protein and not on the recombinant protein. In a specific embodiment, the lectin is *Sambucus Nigra* agglutinin (SNA).

It is further contemplated that the lectin is labeled with a detectable label. In one embodiment, the detectable label is selected from the group consisting of a fluorophore, a radioactive label, an electron-dense reagent, an enzyme, biotin, digoxigenin, a hapten, or a chemiluminescent agent. In a related embodiment, the label is biotin.

It is further contemplated that the sample is derived from a biological sample of a subject. In one embodiment, the sample is a blood sample. In a related embodiment the sample is plasma. In a still further embodiment, the sample is serum.

The invention also provides that the plasma-derived protein and the recombinant protein are essentially the same protein, i.e., have generally the same amino acid structure and function. In one embodiment, the protein is a therapeutic protein, where in various aspects, the protein is selected from the group consisting of a cytokine, a growth factor, a blood clotting factor, an enzyme, a chemokine, a soluble cell-surface receptor, a cell adhesion molecule, an antibody, a hormone, a cytoskeletal protein, a matrix protein, a chaperone protein, a structural protein, a metabolic protein, and any other therapeutic protein known to those of skill in the art. In a further embodiment, the protein is a blood clotting factor. In yet a further embodiment, the blood clotting factor is selected from the group consisting of von Willebrand factor (vWF), Factor VIII (FVIII), Factor VII, and Factor IX (FIX).

In another aspect of the invention, the recombinant protein is produced in a host cell that lacks one or more glycosyltransferases such that the recombinant protein exhibits a different glycosylation pattern compared to the glycosylation pattern of the plasma-derived protein. In various embodiments, the host cell is a bacterial cell, a yeast cell, an insect cell, a plant cell, or a mammalian cell. In a related embodiment the mammalian cell is a Chinese hamster ovary (CHO) cell.

The method of the invention provides for detection of a difference in glycosylation patterns between recombinantly produced protein and naturally-occurring, plasma-derived protein. In one embodiment, the plasma-derived protein comprises a carbohydrate moiety that is not found on the recombinant protein, wherein the carbohydrate moiety is selected from those carbohydrate moieties known in the art and set out herein in the detailed description. In a related embodiment, the plasma-derived protein comprises $\alpha 2,6$-neuraminic acid and the recombinant protein lacks $\alpha 2,6$-neuraminic acid.

In a further aspect of the invention, the method optionally comprises contacting the sample with a binding agent specific for the protein prior to contacting sample with the lectin composition. In one embodiment, the binding agent is a ligand, soluble receptor, an antibody, a monoclonal antibody, a co-factor, or other protein that binds the plasma-derived protein or recombinant protein with specificity.

In a related aspect, the method provides that the binding agent or the plasma-derived protein is bound on a solid support. In various embodiments, the solid support is selected from the group consisting of a filter, a membrane, including a polyvinyl choloride (PVC) membrane, a polyvinylidene fluoride (PDVF) membrane, a polyamide membrane, a plate, including a PVC plate, a polystyrene plate, and any other plate which binds protein, a microcarrier, a macro solid phase bead, a magnetic bead and a polysiloxane/polyvinyl alcohol bead.

In a further embodiment, the protein binding agent or plasma derived protein is in solution.

The method of the invention optionally comprises use of a blocking agent to prevent non-specific binding of the lectin protein to the sample. The method contemplates that the sample is contacted with the blocking agent after contacting of sample with the binding agent. In one embodiment, the blocking agent is selected from the group consisting of serum albumin, gelatin, glycosidase solutions, carbohydrate-modifying agents, such as acetylating agents or methylating agents, and a carbohydrate oxidizing solution. In one embodiment, the carbohydrate oxidizing solution is a periodate solution.

In another aspect of the invention, it is contemplated that a method recited herein utilizes a recombinant protein that is a fragment, variant or analog of the plasma-derived protein.

The invention also provides a method to differentiate plasma-derived protein from recombinant protein in a sample comprising, contacting the sample with a composition comprising a lectin specific for a carbohydrate moiety on the plasma-derived protein; detecting binding of the lectin to the plasma-derived protein; and comparing the amount of binding of protein-bound lectin in the sample to a lectin:protein binding curve to determine the amount of plasma-derived protein in the sample.

In one embodiment, the lectin is *Sambucus nigra* agglutinin (SNA) protein. In a related embodiment, the lectin is labeled with a detectable label as described herein.

In yet another aspect, the invention provides a kit for quantitating levels of plasma derived protein and recombinant protein in a sample, wherein the plasma-derived protein and the recombinant protein encode the same protein, the kit comprising, a binding agent; a composition comprising a lectin specific for a carbohydrate on the plasma-derived protein and a detectable label, and a protein standard. In one embodiment, the kit optionally comprises a blocking agent.

Other features and advantages of the invention will become apparent from the following detailed description. It should be understood, however, that the detailed description and the specific examples, while indicating specific embodiments of the invention, are given by way of illustration only, because various changes and modifications within the spirit and scope of the invention will become apparent to those skilled in the art from this detailed description.

DETAILED DESCRIPTION OF THE INVENTION

The present invention relates, in general, to methods for differentiating plasma-derived protein from recombinantly produced protein in a sample based on the difference in protein glycosylation between the two types of proteins. The invention further contemplates methods to quantitate the amount of plasma-derived protein in a sample comprising both recombinant protein and plasma-derived protein, wherein the plasma-derived protein and the recombinant protein comprise the same, or essentially the same, amino acid sequence.

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that as used in this specification and the appended claims, the singular forms "a," "an," and "the" include plural reference unless the context clearly dictates otherwise.

As used herein, the following terms have the meanings ascribed to them unless specified otherwise.

As used herein a "polypeptide" refers to a polymer composed of amino acid residues linked via peptide bonds. Synthetic polypeptides can be synthesized, for example, using an automated polypeptide synthesizer. The term "protein" typically refers to large polypeptides. The term "peptide" typically refers to short polypeptides. As used herein, polypeptide protein and peptide are used interchangeably.

As used herein a "fragment" of a polypeptide refers to any portion of the polypeptide smaller than the full-length polypeptide or protein expression product. Fragments are typically deletion analogs of the full-length polypeptide wherein one or more amino acid residues have been removed from the amino terminus and/or the carboxy terminus of the full-length polypeptide. Accordingly, "fragments" are a subset of deletion analogs described below.

As used herein an "analog" refers to a polypeptide substantially similar in structure and having the same biological activity, albeit in certain instances to a differing degree, to a naturally-occurring molecule. Analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence. Substitutions can be conservative or non-conservative based on the physicochemical or functional relatedness of the amino acid that is being replaced and the amino acid replacing it.

As used herein a "variant" refers to a protein or analog thereof that is modified to comprise additional chemical moieties not normally a part of the molecule. Such moieties may improve the molecule's solubility, absorption, biological half-life, etc. The moieties may alternatively decrease the toxicity of the molecule and eliminate or attenuate any undesirable side effect of the molecule, etc. Moieties capable of mediating such effects are disclosed in Remington's Pharmaceutical Sciences (1980). Procedure for coupling such moieties to a molecule are well known in the art. For example, the variant may be a blood clotting factor having a chemical modification which confers a longer half-life in vivo to the protein. In certain aspects, variants are polypeptides that are modified by glycosylation, pegylation, or polysialylation.

As used herein, "naturally-occurring," as applied to a protein or polypeptide, refers to the fact that the protein can be found in nature. For example, a polypeptide or polynucleotide sequence that is present in an organism (including viruses) that can be isolated from a source in nature and which has not been intentionally modified by man in the laboratory is naturally-occurring. The terms "naturally-occurring" and "wild-type" are used interchangeably throughout.

As used herein, "plasma-derived," as applied to a protein or polypeptide, refers to a naturally-occurring polypeptide or fragment thereof that is found in blood plasma or serum of a subject. A plasma-derived protein may also be a naturally-occurring protein and a wild-type protein.

As used herein "are the same protein or essentially the same protein" refers to a naturally-occurring protein (e.g., a plasma-derived protein) which may also be expressed recombinantly by genetic engineering, resulting in a recombinant protein having the same or essentially the same amino acid sequence as the naturally derived protein. A recombinant protein which is the same protein as a naturally-produced, plasma-derived protein includes fragments, analogs and variants of the full-length recombinant protein.

As used herein, "expected lectin binding" refers to the hypothetical lectin binding of a sample as determined by assuming that the total amount of protein in the sample is all plasma-derived protein, and extrapolating the amount of lectin binding expected based on the hypothetical amount of plasma-derived protein when compared to a lectin:protein standard binding curve.

As used herein a "detectable moiety," "detectable label" or "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which anti-sera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample.

As used herein the terms "express," "expressing" and "expression" refer to allowing or causing the information in a gene or DNA sequence to become manifest, for example by producing a protein by activating the cellular functions involved in transcription and translation of a corresponding gene or DNA sequence. A DNA sequence is expressed in or by a host cell to form an "expression product" such as a protein. The expression product itself, e.g. the resulting protein, may also be said to be "expressed" or "produced" by the host cell.

Fragments, Variants and Analogs

Methods of the invention are useful to rapidly detect recombinant proteins in a sample, as well as fragments, variants or analogs of the recombinant protein, and further may be useful to detect naturally-occurring protein which may exist as fragments or allelic variants in vivo wherein glycosylation differences can be detected.

Methods for preparing polypeptide fragments, variants or analogs are well-known in the art. Fragments of a polypeptide are prepared using methods well known in the art, including enzymatic cleavage (e.g., trypsin, chymotrypsin) and also using recombinant means to generate a polypeptide fragment having a specific amino acid sequence. Fragments may be generated to comprise a ligand binding domain, a receptor binding domain, a dimerization or multimerization domain, or any other identifiable domain known in the art.

Methods of making polypeptide analogs are also well-known. Analogs may be substantially homologous or substantially identical to the naturally-occurring polypeptide from which the analog is derived, and analogs contemplated by the invention are those which retain at least some of the biological activity of the naturally-occurring polypeptide.

Substitution analogs typically exchange one amino acid of the wild-type for another at one or more sites within the protein, and may be designed to modulate one or more properties of the polypeptide, such as stability against proteolytic cleavage, without the loss of other functions or properties. Substitutions of this kind are generally conservative. By "conservative amino acid substitution" is meant substitution of an amino acid with an amino acid having a side chain of a similar chemical character. Similar amino acids for making conservative substitutions include those having an acidic side chain (glutamic acid, aspartic acid); a basic side chain (arginine, lysine, histidine); a polar amide side chain (glutamine, asparagine); a hydrophobic, aliphatic side chain (leucine, isoleucine, valine, alanine, glycine); an aromatic side chain (phenylalanine, tryptophan, tyrosine); a small side chain (glycine, alanine, serine, threonine, methionine); or an aliphatic hydroxyl side chain (serine, threonine).

Polynucleotide analogs and fragments may be readily generated by a worker of skill to encode biologically active fragments, variants, or mutants of the naturally occurring molecule that possess the same or similar biological activity to the naturally occurring molecule. Routinely practiced methods include PCR techniques, enzymatic digestion of DNA encoding the protein molecule and ligation to heterologous polynucleotide sequences, and the like. For example, point mutagenesis, using PCR and other techniques well-known in the art, may be employed to identify with particularity which amino acid residues are important in particular activities associated with protein activity. Thus, one of skill in the art will be able to generate single base changes in the DNA strand to result in an altered codon and a missense mutation.

It is further contemplated that the protein or polypeptide may be modified to make an analog which is a fusion protein comprising a second agent which is a polypeptide. In one embodiment, the second agent which is a polypeptide is an enzyme, a growth factor, a cytokine, a chemokine, a cell-surface receptor, the extracellular domain of a cell surface receptor, a cell adhesion molecule, or fragment or active domain of a protein described above or of any other type of protein known in the art. In a related embodiment, the second agent is a blood clotting factor such as Factor VIII, Factor VII, Factor IX and von Willebrand factor. The fusion protein contemplated is made by chemical or recombinant techniques well-known in the art.

Protein variants contemplated include polypeptides chemically modified by such techniques as ubiquitination, glycosylation, conjugation to therapeutic or diagnostic agents, labeling (e.g., with radionuclides or various enzymes), covalent polymer attachment such as pegylation (derivatization with polyethylene glycol), introduction of non-hydrolyzable bonds, and insertion or substitution by chemical synthesis of amino acids such as ornithine, which do not normally occur in human proteins. Variants retain the binding properties of non-modified molecules of the invention.

Preparing pegylated variants of a polypeptide, fragment or analogs will generally comprise the steps of (a) reacting the polypeptide with polyethylene glycol (such as a reactive ester or aldehyde derivative of PEG) under conditions whereby the binding construct polypeptide becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-pegylated product. In some embodiments, the binding construct will have a single PEG moiety at the N-terminus. Polyethylene glycol (PEG) may be attached to the protein to provide a longer half-life in vivo. The PEG group may be of any convenient molecular weight and may be linear or branched. The average molecular weight of the PEG will range from about 2 kilo-Dalton ("kDa") to about 100 kDa, more from about 5 kDa to about 50 kDa, most from about 5 kDa to about 10 kDa. The PEG groups will generally be attached to the blood clotting factor via acylation or reductive alkylation through a natural or engineered reactive group on the PEG moiety (e.g., an aldehyde, amino, thiol, or ester group) to a reactive group on the blood clotting factor (e.g., an aldehyde, amino, or ester group).

Additional polypeptide variants useful in the methods of the present invention include polypeptide comprising polysialylate (PSA) moieties. Methods for preparing polysialylated polypeptide are described in United States Patent Publication 20060160948 and Saenko et al., Haemophilia 12:42-51, 2006.

Glycosylation

Glycosylation in human proteins is composed of combinations of simple and complex sugars. Monosaccharides such as mannose, glucose, fucose, galactose, N-acetylgalactosamine, N-acetylglucosamine, and sialic acid/neuraminic acid are combined into linear or branched chains of about two to up to twelve or more monosaccharides (Brooks et al., Expert Rev Proteomics 3:345-59, 2006). Each monosaccharide may be linked to another sugar moiety by either alpha or beta linkages at any of the carbons on the next structure, e.g., α1-3 linkage between first carbon on the first sugar and the third carbon on the next sugar. Addition of sugar moieties is carried out by specific glycosyltransferases and sugars are removed by sugar-specific glycosidase proteins.

In N-glycosylation, the base sugar moiety comprising nine mannose residues, two N-acetylgalactosamine residues and three glucose residues ($GalNac_2Man_9Glc_3$) is attached to an asparagine residue in the protein. Once attached to the protein the oligosaccharide is trimmed to remove the terminal three glucose residues and a mannose residue. The protein is then transported to the Golgi apparatus where further post translational modification takes place, e.g., an additional three mannose moieties are removed leaving a core sugar of five mannose and two N-acetylglucosamine ($Man_5GlcNac_2$). This moiety may be trimmed further or additional residues added. Several higher order oligosaccharides are based off a core structure having three mannose and two N-acetylglucosamine sugars. High mannose contains between five and nine mannose residues linked to the core structure. Complex oligosaccharides comprise N-acetylglucosamine residues substituted for α1,3- and α1,6 linked mannose residues. Hybrid oligosaccharides comprise N-acetylglucosamine residues in place of α1,3-linked mannose residues. Hybrid and complex N-linked oligosaccharides are not synthesized by simple organisms such as yeast and bacteria.

O-glycosylation is a post-translational event that takes place in the Golgi apparatus and begins with linkage of a single monosaccharide, typically N-acetyl galactosamine, but may be a mannose or fucose, to an OH group of a serine or threonine residue. Further chain extension is carried out in a stepwise manner, but there is no core structure required for addition as in N-linked glycosylation (Brooks et al., supra).

Bacteria attach sugar residues to proteins in a wholly different manner than the process in mammalian cells due to a lack of Golgi apparatus other organelles. Most bacterial glycoproteins lack sialic acid moieties in N-glycosylated proteins, or if sialic acid is present, the residues often occur in polysialic acid chains similar to those produced in human neural cell proteins (Brooks et al, supra), but not in typical glycoproteins. The enzyme α2,3 sialyltransferase, responsible for attaching α2,3 sialic acid, has been isolated in *N. gonorrhoeae*. Genetic engineering has been attempted to introduce either bacterial or human glycosyltransferases into bacterial cells in an attempt to produce proteins having glycosylation more similar to that of human proteins. In O-linked glycosylation, bacterial O-glycans are highly methylated and contain the sugar rhamnose which is not found in humans. Also, the first monosaccharide added need not be GalNac.

Yeast (e.g., *Pichia pastoris, S Cerevisiae*) carry out the first stages of N-glycosylation similar to human cells, generating the nine mannose, three glucose, two N-acetylglucosamine core oligosaccharide and attaching it to the protein. The nine-mannose core is then trimmed to only an eight mannose, two N-acetylglucosamine core. This eight-mannose structure is not trimmed as in human cells, but may be further mannosylated to contain up to 100 mannose residues (Brooks et al., supra). Engineered *Pichia pastoris* cells have been developed which express glycosyltransferase enzymes which attach sugar residues in a manner that more closely resembles attachment in human proteins (Brooks et al., supra, Gemgross et al., Nat Biotechnol. 22:1409-14, 2004; Wildt et al., Nat Rev Microbiol 3:119-128, 2005). However, successful introduction of sialyltransferase enzymes has not been achieved, leaving most proteins produced in yeast cells lacking sialyl residues (Brooks et al., supra). Yeast O-glycosylation begins with a mannose residue linked to a serine or threonine residue, and may be extended up to five mannose residues in either a branched or linear configuration. Mannose-linked O-glycosylation does not occur in humans.

Plant cell protein glycosylation differs widely from that in humans. N-glycosylation in plant cells begins like that in human cells, in which a core oligosaccharide $GalNac_2Man_9Glc_3$ is formed. This core structure is then trimmed to a moiety having five to nine mannose residues and two N-acetylglucosamine residues ($Man_{5-9}GlcNac_2$) that may be further extended using sugars such as fucose and xylose (a non-human sugar) in linkage arrangements which are not expressed in human cells and can be immunogenic to humans. Plant glycoproteins are generally thought to be unsialylated, but may be induced to add sialyl groups in culture (Saint-Jore-Dupas et al., Trends in Biotechnol 25: 317-23, 2007). Recently attempts have been made to produce engineered plant cells which express the necessary machinery to produce sialylated proteins (Paccalet et al., Plant Biotechnol. J 5:16-25, 207). In order for plants to express sialic acid, the entire group of human genes responsible for this glycosylation, including sialic acid synthetases, glycosyltransferases and transporters, must be transduced into plant cells, making expression of sialylated plant proteins difficult. Plant O-linked glycosylation may be attached at serine, threonine or hydroxyproline residues. O-linked glycans in plant include the sugars rhamnose, arabinose and glucuronic acid which are not found in humans, as well as more mammalian-type structures, such as GalNac.

Glycosylation in insect cells proceeds similarly to that in plant cells. The N-glycan precursor core is synthesized and added to proteins and trimmed to the tri-mannose core structure. However, further modification is generally restricted to addition of mannose or fucose residues (Brooks et al. supra, Altmann et al., Glycoconjugate J 16:109-123, 1999). Insect cells characteristically produce unsialylated proteins, but may be induced to produce sialyl acid in certain culture conditions, and during certain stages of development (Brooks et al., supra; Tomiya et al., Glycoconj J. 21:343-360, 2004). Insect cells have been engineered to express human sialyltransferase genes with moderate success at generating sialylated proteins (Aumiller et al., Glycobiology 13:497-507, 2003). However, insect cells secrete a sialidase enzyme which can cleave of any sialic acid moieties added to the proteins. O-linked glycosylation is similar to that in humans.

Glycosylation in non-human mammalian cells, such as baby hamster kidney (BHK) and Chinese hamster ovary (CHO) cells, which are the most prevalent cell lines to produce therapeutic proteins on a large scale, often produce proteins with glycosylation moieties similar to human protein, but not exactly the same. For example CHO cells express a different sialic-acid-like sugar moiety and therefore do not produce sialic acid as produced in human cells (Brooks et al., Ext Rev Proteomics 3:345-59, 2006); Chenu et al., Biochem Biophys Acta 1622:133-44, 2003). Further, CHO cells assemble the sialic acid like sugar in an α2,3 configuration which is not expressed in human cells. Modified CHO cells engineered to express the human α2,6 sialyltransferase successfully produce proteins expressing both a human-type α2,6 sialic acid and the hamster-derived α2,3 sialic acid (Bragonzi et al., Biochem Biophys Acta 1474:273-82, 2000). Little is known about O-glycosylation in insects. Insects are believed to O-glycosylate threonine residues, and can include such mammalian-like sugars such as GalNac, and the disaccharide GalNac plus galactose.

Lectin Proteins

Sugar moieties are specifically bound by lectin proteins, which are carbohydrate-binding proteins or glycoproteins which are highly specific for particular sugar moieties. Lectin proteins were first isolated from plant species, e.g., the lectin Sambucus nigra agglutinin (SNA) is isolated from the elderberry tree, and specifically binds α2,6 sialic acid moieties (Brink an-Van der Linden et al., Analytical Biochemistry 303:98-104, 2002). Lectin proteins are also now known to be found in almost all species.

The binding of lectins to their corresponding carbohydrates can be either $Ca^{2+}$-dependent or $Ca^{2+}$-independent. See U.S. Pat. No. 5,225,542. The specificity of the lectin recognition of carbohydrates is highly specific and thus comparable to the antigen-specificity of antibodies or the substrate-specificity of enzymes. For example, several $Ca^{2+}$-independent lectins have been isolated from bovine pancreas and which can specifically the β-galactosides lactose and asialofetuin and the α-galactoside melibiose, and to $Ca^{2+}$-dependent fuscose binding lectins have also been identified.

The lectin Maackia amurensis agglutinin (MAA, MAL) binds α2,3 sialic acid, Sambucus nigra agglutinin (SNA) binds α2,6 sialic acid, Aleuria aurantia lectin (AAL) (Kobata and Yamashita, 1993) and Lens culinaris (LcH) (Yamashita et al., 1993) bind fucose residues. Several plant lectins are specific for N-acetyl-β-D-galactosamine, which is a blood group specific carbohydrate, and are used in blood group typing. C-type animal lectins bind N-Acetylgalactosamine. Limulin and Limax flavus agglutinin (LFA) strongly interact with O-chain glycoproteins. (Fischer et al., Glycoconjugate J. 12:707-13, 2004). In addition, lectin analogs have been developed to mimic the action of natural analogs, but with greater specificity (Ferrand et al., Science 318:619-622, 2007).

The tables* below detail known lectins and their binding specificity useful in the methods of the invention.

| | Lectin name | Organism | Binding Specificity |
|---|---|---|---|
| | | Mannose binding lectins | |
| Con A | Concanavalin A | Canavalia ensiformis | branched α-mannosidic structures; high-mannose type, hybrid type and biantennary complex type N-Glycans |
| LCH | Lentil lectin | Lens culinaris | Fucosylated core region of bi- and triantennary complex type N-Glycans |
| GNA | Snowdrop lectin | Galanthus nivalis | α 1-3 and α 1-6 linked high mannose structures |
| | | Galactose/N-acetylgalactosamine binding lectins | |
| RCA | Ricinus communis Agglutinin, $RCA_{120}$ | Ricinus communis | Galβ1-4GlcNAcβ1-R |
| PNA | Peanut Agglutinin | Arachis hypogaea | Galβ1-3GalNAcα1-Ser/Thr (T-Antigen) |
| AIL | Jacalin | Artocarpus integrifolia | (Sia)Galβ1-3GalNAcα1-Ser/Thr (T-Antigen) |
| VVL | Hairy vetch lectin | Vicia villosa | GalNAcα-Ser/Thr (Tn-Antigen) |
| | | Sialic acid/N-acetylglucosamine binding lectins | |
| WGA | Wheat Germ agglutinin | Triticum vulgaris | GlcNAcβ1-4GlcNAcβ1-4GlcNAc, Neu5Ac (sialic acid) |
| SNA | Elderberry lectin | Sambucus nigra | Neu5Acα2-6Gal(NAc)-R |
| MAL | Maackia amurensis lectin | Maackia amurensis | Neu5Ac/Gcα2-3Galβ1-4GlcNAcβ1-R |
| | | Fucose binding lectins | |
| UEA | Ulex europaeus agglutinin | Ulex europaeus | Fucα1-2Gal-R |
| AAL | Aleuria aurantia lectin | Aleuria aurantia | Fucα1-2Galβ1-4(Fucα1-3/4)Galβ1-4GlcNAc; $R_2$-GlcNAcβ1-4(Fucα1-6)GlcNAc-$R_1$ |

| Lectin name | Abbreviation | Binding Specificity |
|---|---|---|
| Agaricus bisporus | ABA | Fetuin; Galβ1-3GalNAc |
| Amaranthus caudatus | ACL | Galβ 1-3GalNAc, Neu5Acα2-3Galβ 1-3GalNAc; T-Antigen |
| Griffonia simplicifolia lectin I | GSL I | α-N-acetylgalactosamine, α-galactose |

-continued

| Lectin name | Abbreviation | Binding Specificity |
|---|---|---|
| Griffonia simplicifolia lectin II | GSL II | terminal-$\alpha,\beta$-GlcNAc; glycogen |
| Griffonia simplicifolia I B4 | GSL I B4 | $\alpha$-D-galactosyl residues |
| Bauhinia purpurea alba | BPL | Gal$\beta$1-3GalNAc |
| Codium fragile | CFL | GalNAc |
| Datura stramonium | DSL | (GlcNAc$\beta$1-4)$_3$GlcNAc = (Glc$\beta$1-4)$_2$GlcNAc > Glc$\beta$1-4GlcNAc >> GlcNAc |
| Dolichos biflorus | DBA | terminal FP > GalNAc$\alpha$1-3GalNAc > GalNAc$\alpha$1-3Gal; blood group A$_f$ (Forssman pentasaccharide: GalNAc$\alpha$1-3GalNAc$\alpha$1-3Galf$\beta$1-4Gal$\beta$1-4GlcNAc) |
| Erythrina coralldendron | ECor A | GalNAc/N-acetyllactosamin/Lactose/D-Gal |
| Euonymos europaeus | EEA | Gal$\alpha$1-3(L-Fuc$\alpha$1-2)Gal$\beta$1,3/4-$\beta$-GlcNAc; Gal$\alpha$1-3Gal; blood group H structures |
| Glycine max | SBA | terminal $\alpha,\beta$GalNAc > $\alpha,\beta$Gal |
| Helix aspersa | HAA | terminal $\alpha$GalNAc residues |
| Helix pomatia | HPA | GalNAc$\alpha$1-3GalNAc > $\alpha$-GalNAc > $\alpha$-GlcNAc >> $\alpha$-Gal |
| Hippeastrum hybrid | HHL | ($\alpha$1,3)/($\alpha$1,6) mannose; polymannose structures; yeast galactomannans |
| Lotus tetragonolobus | LTL | $\alpha$-L-fucose |
| Lycopersicon esculentum | LEL | (GlcNAc$\beta$ 1-4)$_3$ GlcNAc > (GlcNAc$\beta$1-4)$_2$ GlcNAc > GlcNAc$\beta$1-4GlcNAc |
| Maclura pomifera | MPA | terminal Gal$\beta$1-3GalNAc > GalNAc$\alpha$ 1-6Gal |
| Narcissus pseudonarcissus | NPA | terminal and internal $\alpha$-D-mannosylresidues on glycoconjugates, preferably oligomannoses containing $\alpha$1-6 linkages |
| Phaseolus coccineus | PCA | agglutination is not inhibited by monosaccharides but is inhibited by fetuin |
| Phaseolus vulgaris L | PHA-L | GlcNAc$\beta$1,2Man, triantennary complex oligosaccharides |
| Phaseolus vulgaris E | PHA-E | Gal$\beta$1,4GlcNAc$\beta$1,2Man$\alpha$1,6 |
| Phytolacca americana | PWM | N-acetyl-$\beta$-D-glucosamine oligomers |
| Pisum sativum | PSA, PEA | branched $\alpha$-man, complex type with N-acetylchitobiose-linked core $\alpha$-fuc |
| Psophocarpus tetragonolobus I | PTL, WBA | $\alpha$-galactosamine |
| Solanum tuberosum | STA | N-acetyl-$\beta$-D-glucosamine oligomers |
| Sophora japonica terminal | SJA | Gal$\beta$1,3GalNAc > Gal$\beta$ 1,3GlcNAc > $\alpha\beta$,GalNAc > $\alpha\beta$,Gal |
| Wisteria floribunda | WFA, WFL | terminal N-acetylgalactosamine-$\alpha$- or $\beta$-3 or 6-galactose |

*Tables adapted from Galab Technologies GmbH, Germany, citing Gabius, H.-J.; Gabius, S. (Eds.): Glycosciences-Status and Perspectives. Weinheim: Chapman & Hall, 1997; Goldstein, et al., Sharon, N.; Goldstein, I. J. (Eds.) The Lectins-Properties, Functions and Applications in Biology and Medicine. Orlando: Academic Press, 1986, S. 33-243; Debray et al., Eur. J. Biochem., 117, 41-55, 1981.

The lectins described above may be used in the methods of the invention to differentiate the glycosylation patterns of two different proteins, which may be dependent on the expression source of the protein. For example, the SNA protein as exemplified in the examples below is useful to specifically bind proteins expressing $\alpha$2,6 sialic acid residues while the MAA protein specifically binds $\alpha$2,3 sialic acid residues.

Recombinant Proteins

Methods for making recombinant proteins are well-known in the art. Methods of producing cells, including mammalian cells, which express DNA or RNA encoding a recombinant protein are described in U.S. Pat. Nos. 6,048,729, 5,994,129, and 6,063,630. The teachings of each of these applications are expressly incorporated herein by reference in their entirety.

A nucleic acid construct used to express a polypeptide or fragment, variant or analog thereof can be one which is expressed extrachromosomally (episomally) in the transfected mammalian cell or one which integrates, either randomly or at a pre-selected targeted site through homologous recombination, into the recipient cell's genome. A construct which is expressed extrachromosomally comprises, in addition to polypeptide-encoding sequences, sequences sufficient for expression of the protein in the cells and, optionally, for replication of the construct. It typically includes a promoter, a polypeptide-encoding DNA sequence and a polyadenylation site. The DNA encoding the protein is positioned in the construct in such a manner that its expression is under the control of the promoter. Optionally, the construct may contain additional components such as one or more of the following: a splice site, an enhancer sequence, a selectable marker gene under the control of an appropriate promoter, and an amplifiable marker gene under the control of an appropriate promoter.

In those embodiments in which the DNA construct integrates into the cell's genome, it need include only polypeptide-encoding nucleic acid sequences. Optionally, it can include a promoter and an enhancer sequence, a polyadenylation site or sites, a splice site or sites, nucleic acid sequences which encode a selectable marker or markers, nucleic acid sequences which encode an amplifiable marker and/or DNA homologous to genomic DNA in the recipient cell to target integration of the DNA to a selected site in the genome (targeting DNA or DNA sequences).

Host cells used to produce recombinant proteins are bacterial, yeast, insect, non-mammalian vertebrate, or mammalian cells; the mammalian cells include, but are not limited to, hamster, monkey, chimpanzee, dog, cat, bovine, porcine, mouse, rat, rabbit, sheep and human cells. The host cells can be immortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), muscle cells, hepatocytes and precursors of these somatic cell types.

Commonly used host cells include: Prokaryotic cells such as gram negative or gram positive bacteria, i.e., any strain of *E. coli, Bacillus, Streptomyces, Saccharomyces, Salmonella*, and the like; eukaryotic cells such as CHO (Chinese hamster ovary) cells; baby hamster kidney (BHK) cells; human kidney 293 cells; COS-7 cells; insect cells such as D. Me1-2, Sf4, Sf5, Sf9, and Sf21 and High 5; plant cells and various yeast cells such as *Saccharomyces* and *Pichia*.

Host cells containing the polypeptide-encoding DNA or RNA are cultured under conditions appropriate for growth of the cells and expression of the DNA or RNA. Those cells which express the polypeptide can be identified, using known methods, and the recombinant protein isolated and purified, using known methods; either with or without amplification of polypeptide production. Identification can be carried out, for example, through screening genetically modified mammalian cells displaying a phenotype indicative of the presence of DNA or RNA encoding the protein, such as PCR screening, screening by Southern blot analysis, or screening for the expression of the protein. Selection of cells having incorporated protein-encoding DNA may be accomplished by including a selectable marker in the DNA construct and culturing transfected or infected cells containing a selectable marker gene under conditions appropriate for survival of only those cells that express the selectable marker gene. Further amplification of the introduced DNA construct can be affected by culturing genetically modified cells under conditions appropriate for amplification (e.g., culturing genetically modified cells containing an amplifiable marker gene in the presence of a concentration of a drug at which only cells containing multiple copies of the amplifiable marker gene can survive).

Recombinant proteins which can be therapeutic proteins include, but are not limited to, cytokines, growth factors, blood clotting factors, enzymes, chemokines, soluble cell-surface receptors, cell adhesion molecules, antibodies, hormones, cytoskeletal proteins, matrix proteins, chaperone proteins, structural proteins, metabolic proteins, and other therapeutic proteins known to those of skill in the art. Exemplary recombinant proteins which are/may be used as therapeutics include, but are not limited to, Factor VIII, Factor VII, Factor IX and von Willebrand factor, erythropoietin, interferons, insulin, CTLA4-Ig, alpha-glucocerebrosidase, alpha-glucosidase, follicle stimulating hormone, anti-CD20 antibody, anti-HER2 antibody, anti-CD52 antibody, TNF receptor, and others known in the art. See, for example, Physicians Desk Reference, $62^{nd}$ Edition, 2008, Thomson Healthcare, Montvale, N.J.

Methods of Detecting Protein in a Sample

Therapeutic proteins are often difficult to detect in serum samples due to their similarity to the endogenously produced, naturally-occurring protein. However, it is often beneficial to determine the amount of a therapeutic polypeptide, fragment, variant or analog thereof that has been administered to assess whether the therapeutic protein exhibits desired characteristics such as greater solubility or stability, resistance to enzyme digestion, improved biological half-life, and other features known to those skilled in the art. The method also allows for detection of authorized uses of therapeutic proteins which may be protected by intellectual property rights.

The present invention provides a method to differentiate plasma-derived naturally-occurring proteins from recombinant proteins in a sample, thereby allowing quantitation of each type of protein in a sample. The ability to identify the amount of recombinant protein in a sample over time aids in determination of the optimal therapeutic based on half-life, absorption, stability, etc. The detection assay may be an enzyme linked immunosorbant assay (ELISA), a radioimmunoassay (RIA), a scintillation proximity assay (SPA), surface plasma resonance (SPR), or other binding assays known in the art.

The methods of detection set out herein utilize the difference in glycosylation patterns between plasma-derived proteins and that of many recombinantly produced proteins, as described above.

In order to detect plasma-derived protein in a sample, the sample is contacted with a composition comprising a lectin protein described herein that is specific for a carbohydrate moiety on the plasma-derived protein, and the amount of lectin-bound plasma-derived protein is measured. In one aspect, the contacting step is performed in a liquid environment such as an aqueous buffer, such as phosphate buffered saline (PBS), magnesium/calcium-free PBS, or other appropriate buffers as known in the art. See, for example, Current Protocols in Protein Science, Coligan et al., Eds., 1998, John Wiley and Sons, Hoboken, N.J. It is contemplated that contacting in the method of the invention is carried out for a time period sufficient for binding to reach equilibrium and typically for a time in the range of 15 minutes to overnight. For example, the sample is contacted with the either a binding agent or a lectin protein, for 15 minutes, 30 minutes, 45 minutes, 1 hour, 2 hours, 3 hours, 4 hours, 6 hours, 8 hours, 12 hours, 14 hours, 16 hours, 18 hours, 20 hours, 24 hours, or a time appropriate for sufficient binding for the binding agent or the lectin to the plasma-derived protein.

The method optionally includes at least one or more washing steps, wherein the bound lectin:protein composition is washed prior to measuring protein binding to reduce background measurements caused by unbound polypeptides. Washing of the lectin after incubation of the polypeptide composition and before detection of lectin:protein binding is performed in appropriate buffer plus detergent. Suitable detergents include, but are not limited to alkyldimethylamine oxides, alkyl glucosides, alkyl maltosides, alkyl sulfates (such as sodium dodecyl sulfate (SDS)), NP-40, alkyl thioglucosides, betaines, bile acids, CHAP series, digitonin, glucamides, lecithins/lysolecithins, nonionic polyoxyethylene-based detergents, including TRITON-X, polysorbates, such as TWEEN® 20 and TWEEN® 80, BRIJ®, GENAPOL® and THESIT®, quaternary ammonium compounds, and the like. See also Current Protocols in Protein Science, Appendix 1B, Suppl. 11, 1998, John Wiley and Sons, Hoboken, N.J. Suitable detergents can be determined using routine experimentation (see Neugebauer, J., A Guide to the Properties and Use of Detergents in Biology and Biochemistry, Calbiochem-Novabiochem Corp., La Jolla, Calif., 1988).

As discussed above, the lectin protein may be linked to a detectable moiety or a detectable label. Detectable moiety or label refers to a composition detectable by spectroscopic, photochemical, biochemical, immunochemical, or chemical means. The detectable moiety often generates a measurable signal, such as a radioactive, chromogenic, or fluorescent signal, that can be used to quantitate the amount of bound detectable moiety in a sample. The detectable moiety can be incorporated in or attached to the protein either covalently, or through ionic, van der Waals or hydrogen bonds, e.g., incorporation of radioactive nucleotides, or biotinylated nucleotides that are recognized by streptavidin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavidin. The binding partner may itself be directly detectable, for example, an antibody may be labeled with a fluorescent molecule. Selection of a method quantitation of the signal is achieved by, e.g., scintillation counting, densitometry, or flow cytometry.

Examples of labels suitable for use in the assay methods of the invention include, radioactive labels, fluorophores, electron-dense reagents, enzymes (e.g., as commonly used in an ELISA), biotin, digoxigenin, or haptens as well as proteins which can be made detectable, e.g., by incorporating a radiolabel into the hapten or peptide, or used to detect antibodies specifically reactive with the hapten or peptide. Also contemplated are proteins for which antisera or monoclonal antibodies are available, or nucleic acid molecules with a sequence complementary to a target, a nanotag, a molecular mass bead, a magnetic agent, a nano- or micro-bead containing a fluorescent dye, a quantum dot, a quantum bead, a fluorescent protein, dendrimers with a fluorescent label, a micro-transponder, an electron donor molecule or molecular structure, or a light reflecting particle.

Additional labels contemplated for use with present invention include, but are not limited to, fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold, colored glass or plastic beads (e.g., polystyrene, polypropylene, latex, etc.), and luminescent or chemiluminescent labels (e.g., Europium (Eu), MSD Sulfo-Tag).

The label may be coupled directly or indirectly to the desired component of the assay according to methods well known in the art. In a specific embodiment, the label is covalently bound to the component using an isocyanate or N-hydroxysuccinimide ester reagent for conjugation of an active agent according to the invention. In one aspect of the invention, bifunctional isocyanate reagents are used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The compounds useful in the method of the invention can also be conjugated directly to signal-generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds suitable for use as labels include, but are not limited to, those listed above as well as fluorescein derivatives, rhodamine and its derivatives, dansyl, umbelliferone, eosin, TRITC-amine, quinine, fluorescein W, acridine yellow, lissamine rhodamine, B sulfonyl chloride erythroscein, ruthenium (tris, bipyridinium), europium, Texas Red, nicotinamide adenine dinucleotide, flavin adenine dinucleotide, etc. Chemiluminescent compounds suitable for use as labels include, but are not limited to, MSD Sulfa-TAG, Europium (Eu), Samarium (Sm), luciferin and 2,3-dihydrophthalazinediones, e.g., luminol. For a review of various labeling or signal producing systems that can be used in the methods of the present invention, see U.S. Pat. No. 4,391,904.

Means for detecting labels are well known to those of skill in the art and are dictated by the type of label to be detected. Thus, for example, where the label is radioactive, means for detection include a scintillation counter (e.g., radioimmunoassay, scintillation proximity assay) (Pitas et al., Drug Metab Dispos. 34:906-12, 2006) or photographic film, as in autoradiography. Where the label is a fluorescent label, it may be detected by exciting the fluorochrome with the appropriate wavelength of light and detecting the resulting fluorescence (e.g., ELISA, flow cytometry, or other methods known in the art). The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands can be used in the diagnosis of a disease or health condition.

In another embodiment, the sample containing the plasma-derived protein is first contacted with a binding agent (that is not a lectin protein) that binds the protein of interest. The binding agent may be an antibody, a soluble receptor, a ligand, a co-factor, or other protein that binds the plasma-derived protein or recombinant protein with specificity. By "with specificity" is meant that the binding agent may bind a protein with particularity, but does not exclusively bind a target molecule or moiety. "Specifically binds" refers to the ability of a binding agent to recognize and preferentially binds to a defined target protein or other moiety (e.g. carbohydrate).

The method also optionally comprises a blocking step, wherein the binding agent is contacted with a blocking agent prior to contacting with the sample to remove any unwanted sugar moieties from the protein binding agent used to capture or bind the protein. Exemplary blocking agents, include but are not limited to, serum albumin, gelatin, glycosidase solutions, which cleave particular sugar residues, carbohydrate-modifying agents, such as acetylating agents or methylating agents which modify the carbohydrates, a carbohydrate oxidizing solution, such as a periodate solution, and other blocking agents known in the art.

In one embodiment the labeled composition or the binding agent useful in the methods of the invention is linked to a solid support, including but not limited to, filters, plates or membranes. It is further contemplated that the labeled compounds and the binding agents may be labeled and interact in solution. For example, the capture antibody may be labeled with a fluorescent resonance energy transfer (FRET) donor molecule and a second binding agent, such as a lectin protein, is labeled with a FRET acceptor molecule such that the molecules are in proximity when binding occurs. Alternatively, the lectin protein may be labeled with the FRET donor and the protein molecule labeled with the FRET acceptor. Another possibility is to separate quenching and fluorescent molecule both present on the antibody or target when target and antibody hybridize. The molecules are only close enough for the label to emit if they are interacting with the cognate reagent. This produces a system where the molecule only emits when it interacts with the reagent (direct monitoring). A narrow band pass filter can be used to block all wavelengths except that of the molecule's label. FRET molecule pairs are commercially available in the art (e.g., from Invitrogen), and may be used according to the manufacturer's protocol. FRET emissions are detected using optical imaging techniques, such as a CCD camera.

Another method of detecting lectin-plasma-derived protein interactions is to label with an electron donor. This donor label would give electrons to an electrical contact to which the reagent is bound. See, for example, Ghindilis, A. (Biochem Soc Trans. 28:84-9, 2000) and Dai et al. (Cancer Detect Prev. 29:233-40, 2005) which describe enzymes useful in and methods for electro immunoassays. The electron contact would then be read by an A to D (analog to digital) converter and quantified. The higher the electron count the more interactions took place.

One embodiment of a label capable of single molecule detection is the use of plasmon-resonant particles (PRPs) as optical reporters, as described in Schultz et al., *Proc. Nat'l Acad. Sci.*, 97:996-1001 (2000), incorporated herein by reference. PRPs are metallic nanoparticles, typically 40-100 nm in diameter, which scatter light elastically with remarkable efficiency because of a collective resonance of the conduction electrons in the metal (i.e., the surface plasmon resonance). The magnitude, peak wavelength, and spectral bandwidth of the plasmon resonance associated with a nanoparticle are dependent on the particle's size, shape, and material composition, as well as the local environment. By influencing these parameters during preparation, PRPs can be formed that have scattering peak anywhere in the visible range of the spectrum. For spherical PRPs, both the peak scattering wavelength and scattering efficiency increase with larger radius, providing a means for producing differently colored labels. Populations of silver spheres, for example, can be reproducibly prepared for which the peak scattering wavelength is within a few nanometers of the targeted wavelength, by adjusting the final radius of the spheres during preparation. Because PRPs are bright, yet nanosized, they are used as indicators for single-molecule detection; that is, the presence of a bound PRP in a field of view can indicate a single binding event.

Lectin:plasma-derived protein complexes are also detected using nanoparticle-derived techniques. See, for example, Ao et al. (Anal Chem. 78:1104-6, 2006) which describes gold nanoparticle quenching, Chen et al., (Biomaterials 27:2313-21, 2006) which describes SiO(2)/Au nanoparticle surfaces in antibody detection, and Lieu et al. (J Immunol Methods. 307:34-40, 2005), which describes silicon dioxide nanoparticles containing dibromofluorescein for use in solid substrate-room temperature phosphorescence immunoassay (SS-RTP-IA).

For the methods of the invention, the binding agent or plasma-derived protein may be bound to a variety of solid supports, including but not limited to filters, PVC membranes, PDVF membranes, PVC plates and other plates which bind protein, microcarriers, macro solid phase beads, magnetic beads, made out of for example, polystyrene, nanoparticles, such as bimetallic silver-gold nanoparticles (Yan Cui et al., J. Phys. Chem. B, 110:4002-06, 2006), polyamide membrane (PAM) sheets (Sun et al, Analytical Letters 34:1627-37, 2001) and polysiloxane/polyvinyl alcohol beads (Coêlho et al., Biotechnology Letters 24: 1705-1708, 2002).

For example, microspheres with multiple fluorescent molecular fillings, different materials, surface texture, surface patterns, etc. can be utilized as identification tags. It is contemplated that either the capture antibody or the lysosomal enzyme is covalently bound to the bead and reacted against the opposite binding partner to assay the amount of lysosomal enzyme-specific antibody in serum. See, for example, Current Protocols in Immunology, Unit 6.11). Fluorescently filled microspheres are currently available from Molecular Probes, Inc. and other companies. Microspheres as small as 20 nm diameter polystyrene beads are currently available.

The plasma-derived protein or binding agent is attached to the solid support using standard protocols in the art, e.g., as described by the manufacturer of the support, or using standard chemical crosslinking techniques known in the art. See e.g., Pierce Biotechnology, Inc. (Rockford, Ill.) crosslinking kits.

Kits

Kits are also contemplated within the scope of the invention. A typical kit can comprise lectin protein that specifically binds to a plasma-derived protein, such as a blood clotting factor, optionally linked to a detectable label, and a protein standard containing a known quantity of a protein. In one embodiment the kit further comprises a binding agent, which specifically binds the plasma-derived protein, wherein the binding agent is an antibody, a soluble receptor, a ligand, a cofactor (e.g., a second blood clotting factor or a chaperone protein) or another agent that specifically binds the plasma-derived protein. The kit may optionally include reagents for carrying out an immunoassay such as a second binding agent, linked to a detectable label that either binds to a plasma-derived protein or to the lectin protein; if the label is an enzyme, the kit may also include a substrate from which the enzyme releases a detectable signal. It is further contemplated that the kit comprises a blocking agent in order to prevent non-specific binding of the lectin composition.

Additional aspects and details of the invention will be apparent from the following examples, which are intended to be illustrative rather than limiting.

EXAMPLES

Example 1

*Sambucus nigra* Agglutinin (SNA) Binding of Plasma VWF and Recombinant CHO Cell-derived VWF (rVWF)

Human proteins express unique glycosylation patterns compared to proteins produced in other organisms, which presents a difficulty when producing recombinant proteins where glycosylation is important in protein function. One of the most popular cell lines for producing recombinant human protein, Chinese hamster ovary (CHO) cells, lacks the enzyme α2,6 sialyltransferase, which confers addition of α2,6-sialic acid onto complex glycoproteins. While this difference may be minimal affect with respect to interfering with activity of a protein, this difference in glycosylation can be used to distinguish recombinantly produced protein or naturally-produced secreted human proteins. Lectin proteins that distinguish between the different glycosylation patterns can be used in binding assays to determine the levels of recombinant or naturally occurring protein in a biological sample. For example *Sambucus nigra* agglutinin (SNA) binds α2,6 linked neuraminic acid (sialic acid) but not α2,3 neuraminic acid.

To determine if SNA binding could distinguish naturally-occurring human proteins from protein produced recombinantly in CHO cells, plasma derived vWF (pVWF) and recombinantly produced vWF (rVWF) were used in an SNA binding assay.

An enzyme-linked immunosorbent assay (ELISA) is one method for detecting von Willebrand factor antigen (vWF:Ag), which measures the quantity of vWF, independent of vWF function, which usually constitutes vWF complexed with factor VIII. However, this assay cannot differentiate between plasma-derived or recombinant protein. Therefore, a modified form of this assay is used to detect glycosylated vWF.

Briefly, for the glycosylation detection assay, generally, a polyclonal or monoclonal anti-human VWF antibody preparation is bound to polystyrene microplates at slightly alkaline conditions. After blocking with an inert non-glycosylated protein solution, incubation of the samples with periodate oxidation reduces the ability of the coating antibody to bind SNA by removing sialic acid residues on the antibody protein. Several dilutions of human plasma or a rVWF preparation are then loaded to the wells. After a washing step removing non-bound sample components the antibody-bound VWF/rVWF is allowed to react with biotinylated SNA. The bound lectin (SNA) is then detected by reaction with a streptavidin-peroxidase preparation measuring the peroxidase activity with an appropriate substrate.

The following experimental conditions were used to measure either plasma-derived vWF or rVWF carried out in separate assays: 100 μL coating solution (anti-human VWF, (Dako, Denmark), diluted 1/500 in coating buffer 0.1 M Na$_2$CO$_3$, 0.1 M NaHCO$_3$, pH 9.5; alternatively any monoclonal antibody can be used as well in an appropriate dilution) was incubated for 16 hours at 4° C. or for 1 hr at 37° C. in wells of a MAXISORP™ F96 (NUNC, Germany) microplate. After washing in wash buffer (0.8% NaCl, 0.02% KCl, 0.02% KH$_2$PO$_4$, 0.126% Na$_2$HPO$_4$.2H$_2$O, 0.05% Tween 20 [EIA-grade, Bio-Rad, Hercules, Calif.], pH 7.0-7.4) the wells were blocked by incubation with dilution buffer (0.1% gelatin [Bio-Rad, EIA-grade] or 0.1% bovine serum albumin [SIGMA, EIA-grade, St. Louis, Mo.], 2 mM benzamidine hydrochloride in washing buffer) using 200 μL/well for 30 minutes at 37° C. After washing, periodate oxidation was carried out by incubating the wells with 200 μL/well periodate solution (10 mM sodium periodate in 50 mM sodium acetate, pH 5.5) for 30 minutes at room temperature (RT). The washed plate was then incubated for 5 minutes at RT with 200 μl/well ethanolamine solution (1% ethanolamine in water) and washed again.

The sample dilutions were prepared using dilution buffer. For the human plasma pool, a serial dilution series was prepared comprising the dilutions 1/400, 1/800, 1/1600, 1/3200 and 1/6400 corresponding to VWF:Ag concentrations ranging from 2.88 to 0.18 mU VWF:Ag/mL. For the samples containing rVWF, the rVWF preparation was used at higher concentrations (311-19 mU/mL). 100 μL/well were loaded in duplicates to the wells and incubated for 60 minutes at RT. The plate was then washed and 100 μL/well of biotinylated SNA (Vector Laboratories, Burlingame, Calif.) was added at a concentration of 2 μg/mL. The plates were incubated for 60 minutes at RT and washed, and 100 μl/well streptavidin-peroxidase (Dako, diluted 1/4000) was added and incubated for 30 minutes at RT. The incubation was terminated by a washing step. Bound peroxidase was detected by a color reaction with the peroxidase substrate SUREBLUE™ (KPL, Gaithersburg, Md.). 100 μL/well of sample was incubated for 10 to 15 minutes at RT. The reaction was stopped by adding 100 μL/well 1.5 M H$_2$SO$_4$. Subsequently, the plate was measured with an ELISA reader at 450 nm with the reference wavelength set to 620 nm. For further data evaluation, a linear regression analysis was performed using the blank corrected mean values of the optical densities measured and the VWF:Ag concentrations of the dilutions of the plasma pool. The calibration curve obtained is used to calculate the SNA binding of unknowns relative to that obtained for the plasma pool, which was set at 100%.

The analysis of plasma VWF resulted in a clear dose dependent relation between the VWF:Ag concentration and the SNA-binding measured. This relation was highly linear ($R^2$=0.9996) within the defined range of 0.2 to 2.9 mU VWF:Ag/ml allowing the construction of a linear calibration curve. In contrast to plasma VWF, CHO cell-derived rVWF showed no binding to SNA even when 100 times higher concentrations were used. Thus, the preparations can be differentiated by their different reactivity with SNA. Similar results were obtained using a monoclonal anti-human VWF with a defined binding epitope in the A1 domain of human VWF. These differences in reactivity towards SNA reflect the fact that CHO cell-derived rVWF contains no α2,6-linked neuraminic acid, which is the glycan structure specifically required for binding to SNA.

Example 2

SNA Binding of Plasma Factor IX (pFIX) and Recombinant CHO-cell Derived Factor IX (rFIX)

In order to determine if the reactivity of the plasma-derived VWF:Ag with SNA is unique to the plasma VWF, a second CHO-derived blood clotting factor, Factor IX (FIX), was analyzed in an SNA binding assay.

A polyclonal anti-human FIX antibody preparation was bound to polystyrene microplates as above. For the human plasma pool, a geometric dilution series was prepared in dilution buffer using the dilutions 1/320, 1/640, 1/1280, 1/2560 and 1/5120 corresponding to FIX:Ag concentrations ranging from 3.09 to 0.19 mU FIX:Ag/mL. The rFIX preparation was investigated at higher concentrations (78-4.9 mU/mL). 100 μL/well were loaded to the wells in duplicates and incubated for 60 minutes at RT, and development carried out as described previously.

Similar to the results with the plasma VWF protein, there was a clear dose dependent relation between the plasma FIX:Ag concentration and the SNA binding measured. This relation was linear ($R^2$=0.9963) within the defined range of 0.2 to 3.1 mU FIX:Ag/ml allowing the construction of a calibration curve. In contrast to plasma FIX, CHO-cell derived rFIX showed no binding to SNA even at the 10 times higher concentrations investigated. Thus, both preparations can be differentiated by their different reactivity with SNA.

Example 3

Measurement of SNA Binding of Plasma VWF and CHO Cell-derived rVWF After Neuraminidase Treatment To ensure that the binding to SNA was specific for SNA, the specificity of the binding to SNA was investigated using the enzyme neuraminidase, which cleaves off or desialylates both $\alpha 2,6$ and $\alpha 2,3$ neuraminic acid from oligosaccharides. After incubating antibody-bound plasma VWF and rVWF with increasing levels of neuraminidase on the microtiter plate, the effects of neuraminidase desialylation on the SNA binding of pVWF and rVWF were measured.

The anti-VWF microtiter plates were prepared for analysis as described previously. Both the human plasma pool and the rVWF preparation were diluted to obtain VWF:Ag concentrations of 5 mU/mL and 2.5 mU/mL. 100 µL/well of these dilutions were loaded to the coated, periodate-oxidized plates and incubated for 60 minute at RT and washed afterwards. The neuraminidase digest was then carried out on the plate with the plasma-derived vWF and rVWF immobilized by the bound antibody. Neuraminidase (Sigma, St. Louis, Mo.) was used at the concentrations of 0, 1, 5, 10 and 20 mU/mL, obtained by diluting the enzyme with 20 mM Bis-Tris-Propane containing 2 mg/mL bovine serum albumin. 100 µL/well neuraminidase solution was incubated for 2 hours at 37° C. Afterwards, the plates were washed and incubated with biotinylated SNA (Vector; 2 µg/mL; 100 µL/well) for 60 minutes at RT. This incubation was terminated by washing before the plates were incubated 30 minutes at RT with streptavidin peroxidase (Dako, 1/4000). After a final washing step, the bound peroxidase activity was measured with the peroxidase substrate SUREBLUE™ as above.

Results show that, whereas CHO-cell derived VWF shows no binding to SNA in the SNA assay, this binding is not altered after treatment with neuraminidase, however, the SNA binding of plasma VWF is reduced proportional to the concentration of the neuraminidase applied. This result was observed with both VWF:Ag concentrations investigated. At a neuraminidase concentration of 20 mU/mL and under the experimental conditions applied, the SNA binding is less than 95% of the initially measured concentration.

These results showed that the SNA protein specifically bound to $\alpha 2,6$ N-acetylneuraminic acid, since removal of neuraminic acid from the plasma-derived protein caused loss of binding. CHO cell derived rVWF showed no binding to SNA with and without neuraminidase treatment because the neuraminic acid is present only in a linkage which is not recognized by SNA or hydrolyzed with neuraminidase.

Example 4

Measurement of Binding of Plasma VWF and CHO Cell-derived rVWF after Neuraminidase Treatment to the Lectin *Maackia Amurensis* Agglutinin (MAA)

Because rVWF does not bind SNA due to the lack of $\alpha 2,6$-linked neuraminic acid, removing neuraminic acid was not expected to alter binding of SNA to rVWF. In order to confirm that the recombinant protein did express sialic acid moieties, but in a different configuration than the plasma derived sialic acid, a binding assay that measures binding of protein to $\alpha 2,3$-linked neuraminic acid is used to detect the recombinantly expressed $\alpha 2,3$-linked neuraminic acid on the recombinant protein. The lectin, *Maackia amurensis* agglutinin (MAA), which binds $\alpha 2,3$-linked neuraminic acid, was used to determine if desialylation of rVWF occurred in the presence of neuraminidase. After incubating antibody-bound plasma VWF and rVWF with increasing levels of neuraminidase, the binding of the proteins to MAA was measured.

Anti-vWF plates were prepared as above. Both the human plasma pool and the rVWF preparation were diluted to obtain VWF:Ag concentrations of 5 mU/mL and 2.5 mU/mL. 100 µL/well of the sample dilutions were loaded to the coated, periodate-oxidized plates and incubated for 60 minutes at RT and washed afterwards. The neuraminidase digest was then carried out on the plate. Neuraminidase (Sigma) was used at the concentrations of 0, 1, 5, 10 and 20 mU/mL. Afterwards, the plates were washed and incubated with the biotinylated MAA (Vector, 1 µg/mL) for 60 minutes at RT. The incubation was terminated by washing, after which the plates were incubated 30 minutes at RT with streptavidin peroxidase (DakoCytomation, 1/4000). After a final washing step, the bound peroxidase was measured as previously described.

Recombinant vWF was bound by the MAA lectin indicating the presence of sialic acid on the recombinant protein. Addition of neuraminidase to the culture wells abolished both the plasma VWF and the rVWF binding to MAL, which recognizes neuraminic acid when present in $\alpha 2,3$-linkage. Even the lowest enzyme concentration tested showed a reduction of >95% of the MAL binding. Similar data were obtained when VWF was used at a concentration of 2.5 mU/mL. Thus, effective desialylation also occurred for the rVWF preparation detectable only when using MAL, but undetectable when SNA is applied indicating the specificity of SNA binding to plasma VWF and not recombinant VWF.

Example 5

Inhibition of the SNA Binding to Plasma VWF and CHO Cell-derived Recombinant VWF (rVWF) with 6'-Sialyllactose Lectins bind specifically to monosaccharides or oligosaccharides, which can either be free in solution or as part of larger oligosaccharides found on glycoproteins, glycolipids or other glycoconjugates. The specificity of the lectin binding can be investigated by inhibition studies using these mono- or oligosaccharides in competition binding assays. The trisaccharide 6'-sialyllactose is known to be a potent inhibitor of the binding of the lectin SNA and was used to confirm the specificity of the binding of SNA to plasma VWF.

Anti-vWF plates were coated and prepared as above. The human plasma pool samples were diluted to obtain a VWF:Ag concentration of 5 mU/mL. 100 µL/well was loaded and incubated for 60 minutes at RT. 50 µL 6-sialyllactose (Sigma, A-9204) was added to the plate at concentration ranging from 2.1 to 150 µM and then 50 µL of the biotinylated SNA (Vector, 1 µg/mL) was added and incubated for 60 minutes at RT. The incubation was terminated by washing, after which the plates were incubated 30 minutes at RT with streptavidin peroxidase (DakoCytomation, 1/4000). After a final washing step, the bound peroxidase was measured as previously described.

The trisaccharide 6'-sialyllactose showed concentration-dependent inhibition of the binding of SNA to plasma VWF under the experimental conditions used, demonstrating approximately 25% inhibition at 10 µM 6'-sialyllactose and 75% inhibition at 100 µM 6'-sialyllactose. This observation confirmed that the measured binding was dependent on the N-glycan structures of plasma VWF and was not caused by any other reaction.

Example 6

Inhibition of the SNA Binding to Plasma VWF and CHO Cell-derived Recombinant VWF (rVWF) with 3'-Sialyllactose Another trisaccharide, 3'-sialyllactose, in which the neuraminic acid is linked α2,3 to the galactose residue of the lactose, would be expected to show no effects on the binding of SNA to plasma VWF since plasma VWF lacks α2,3 sialic acid. To examine the specificity of binding, the effects of 3'-sialyllactose on plasma-derived protein and CHO-derived recombinant protein was measured.

VWF-Ag specific plates were prepared as above and the 3' siallylactose inhibition assay performed as described for the 6' sialyllactose assay in Example 5 above. Results demonstrated that 3'-sialyllactose had no effect on the binding of SNA to plasma VWF, confirming that SNA binds to neuraminic acid only when present in α2,6-linkage.

Example 7

4-point calibration curve for the measurement of CHO Cell-derived Recombinant VWF (rVWF) in the Presence of Plasma VWF In order to determine if the SNA binding assay could allow quantitation of the amount of plasma derived protein compared to recombinant protein in a single sample, test samples comprising both the plasma VWF and recombinant VWF were analyzed for SNA binding and a calibration curve developed for quantitation of rVWF in the samples.

Briefly, a human normal plasma pool containing VWF:Ag at a concentration of approximately 1 U/mL was spiked with 0, 0.2, 0.5, 1.0 and 2.0 U rVWF. The VWF:Ag concentration and the SNA binding of these samples was measured in six independent test units. The SNA binding measured for a separate, non-spiked human plasma pool was used as basis to calculate an expected, hypothetical SNA binding for the spiked samples under the assumption that the VWF:Ag present in these samples would be plasma VWF only. The difference between these hypothetically calculated SNA binding values and the measured values was calculated, which reflects the amounts of rVWF in mixture with the plasma VWF. To verify this assumption, the differences in binding were then plotted against the amount of rVWF contained in these samples and a linear regression analysis was performed. Thus, a calibration curve was obtained allowing for determination of the concentrations of rVWF in the presence of plasma VWF.

The anti-vWF microtiter plates were prepared as above. For the calibration curve, a sample dilution series comprising the dilutions 1/100, 1/200, 1/400, 1/800 and 1/1600 was prepared using a human plasma pool. Samples were diluted to obtain VWF:Ag concentrations within the range covered by this calibration curve. 100 µL/well of these dilutions were loaded, incubated for 15 minutes at RT before 100 µl/well of the detection antibody (rabbit anti-human VWF-peroxidase, Dako, 1/2000) was added. This incubation was carried out for 60 minutes at RT and terminated by washing. The bound peroxidase activity was measured with SUREBLUE™ peroxidase substrate. The color reaction was stopped using 1.5 M sulfuric acid. The plates were measured subsequently with an ELISA reader at 450 nm with the reference wavelength set at 650 nm. The VWF:Ag concentration of these samples was then obtained in U/mL after extrapolation on the calibration curve.

The SNA binding of the samples was measured using anti-vWF plates prepared as above. The sample dilutions were prepared using dilution buffer. For the calibration curve a dilution series comprising the dilutions 1/400, 1/800, 1/1600, 1/3200 and 1/6400 was prepared using a human plasma pool. Samples were diluted to obtain SNA binding within the concentration range covered by this calibration curve. 100 µL/well of each dilution was loaded to the coated, periodate-oxidized plates and incubated for 60 minutes at RT. Afterwards, the plates were washed and incubated with biotinylated SNA, and SNA binding measured as previously described.

Table 1 shows data obtained in the six independent test units for the VWF:Ag concentration and the SNA binding of these samples.

TABLE 1

VWF: Ag and SNA binding of spiked samples

| | CHO-cell derived rVWF spiked to human plasma | | | | |
|---|---|---|---|---|---|
| | 0 U | 0.2 U | 0.5 U | 1.0 U | 2.0 U |
| VWF:Ag | | | | | |
| Test 1 | 0.93 | 1.11 | 1.49 | 2.07 | 3.18 |
| Test 2 | 0.94 | 1.11 | 1.47 | 1.95 | 3.21 |
| Test 3 | 0.91 | 0.99 | 1.26 | 1.93 | 2.98 |
| Test 4 | 0.92 | 1.06 | 1.32 | 1.99 | 3.14 |
| Test 5 | 0.88 | 1.05 | 1.29 | 1.92 | 3.06 |
| Test 6 | 0.91 | 1.08 | 1.30 | 1.56 | 3.50 |
| Mean | 0.92 | 1.07 | 1.36 | 1.90 | 3.18 |
| SD | 2.3 | 4.2 | 7.3 | 9.3 | 5.6 |
| SNA binding | | | | | |
| Test 1 | 130.1 | 99.0 | 81.1 | 52.4 | 34.5 |
| Test 2 | 125.3 | 105.2 | 76.6 | 56.7 | 33.1 |
| Test 3 | 135.0 | 119.8 | 104.3 | 62.5 | 37.2 |
| Test 4 | 135.4 | 111.1 | 87.0 | 63.0 | 38.3 |
| Test 5 | 152.0 | 98.1 | 87.9 | 54.2 | 33.0 |
| Test 6 | 145.3 | 107.6 | 91.7 | 73.4 | 34.0 |
| Mean | 137.2 | 106.8 | 88.1 | 60.4 | 35.0 |
| SD | 7.2 | 7.6 | 10.9 | 12.8 | 6.3 |

The SNA binding of the samples was obtained after extrapolation from a SNA:protein binding calibration curve and levels are expressed relative to that of the human plasma pool which was not spiked with recombinant protein, defined as 100% SNA binding. Plasma VWF at mean concentration of 0.92 U had a mean SNA binding corresponding to 137.2% of that measured for a human plasma pool. Using this mean SNA binding as measured for the human plasma sample containing no rVWF, the hypothetical SNA binding was calculated for the spiked samples under the assumption that the VWF:Ag measured was only plasma VWF. Results are shown in Table 2.

TABLE 2

Calculation of the hypothetical SNA binding for the plasma samples spiked with rVWF

| | CHO cell-derived rVWF spiked to human plasma | | | | |
|---|---|---|---|---|---|
| | 0 | 0.2 | 0.5 | 1.0 | 2.0 |
| Total VWF | 0.92 | 1.07 | 1.36 | 1.90 | 3.18 |
| rVWF | — | 0.15 | 0.44 | 0.99 | 2.26 |

TABLE 2-continued

Calculation of the hypothetical SNA binding
for the plasma samples spiked with rVWF

| | CHO cell-derived rVWF spiked to human plasma | | | | |
|---|---|---|---|---|---|
| | 0 | 0.2 | 0.5 | 1.0 | 2.0 |
| SNA binding expected | 137.2 | 159.9 | 203.2 | 285.4 | 476.6 |
| SNA binding measured | 137.2 | 106.8 | 88.1 | 60.4 | 35.0 |
| Difference | 0.0 | 53.1 | 115.1 | 225.0 | 441.6 |
| SD | | 4.0 | 12.5 | 28.7 | 28.0 |

Figure 1:
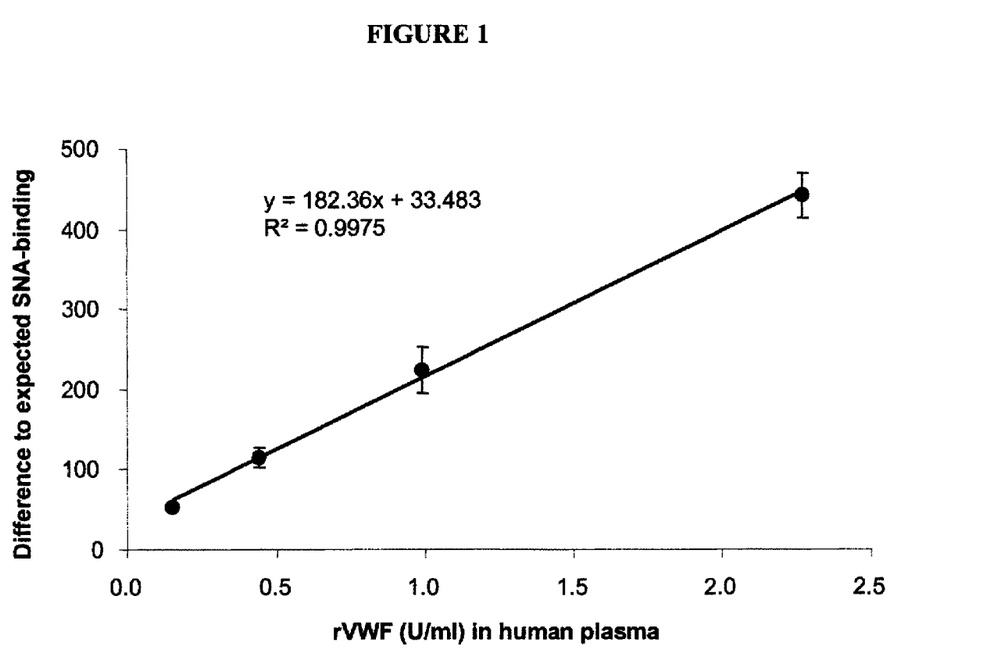
FIG. 1 is a plot of a four-point calibration curve correlating the difference in expected and observed SNA binding in a sample with the amount of recombinant protein.

The difference between the calculated binding and the expected SNA binding correlated well with the concentrations of CHO cell derived rVWF spiked into the human plasma samples within the range investigated in this experiment. A good linear relationship was observed, when 0.2 to 2.0 U rVWF were added to a sample already containing 1 U VWF:Ag, wherein increasing concentrations of recombinant vWF in the sample resulted in larger differences in expected binding. A plot of the calibration curve correlating the difference in SNA binding with the amount of recombinant protein is shown in FIG. 1. These results show that the assay provides a reliable method for differentiating between plasma-derived and recombinant protein in a sample and determining the levels of each type of protein in a single sample.

Example 8

8-point calibration curve for the measurement of CHO Cell-derived Recombinant VWF (rVWF) in the Presence of Plasma VWF An additional quantitative assay was developed for increased sensitivity in measuring the amount of plasma derived protein and recombinant protein in a sample.

A human normal plasma pool containing VWF:Ag at a concentration of approximately 1 U/mL was spiked with 0, 0.2, 0.4, 0.5, 0.6, 0.8, 1.0, 1.2 and 1.5 U rVWF. The VWF:Ag concentration and the SNA binding of these samples was measured in six independent test units. The SNA binding measured for the non-spiked human plasma pool was used as basis to calculate an expected, hypothetical SNA binding for the spiked samples as in Example 7.

The VWF-specific plates were prepared as above. For the calibration curve, a dilution series comprising the dilutions 1/100, 1/200, 1/400, 1/800 and 1/1600 was prepared using a human plasma pool, and the VWF:Ag concentration and SNA binding measured as in Example 7. The SNA binding of the samples was obtained after extrapolation on the calibration curve and levels are expressed relative to that of the human plasma pool, defined as 100% SNA binding. Table 3 shows the measuring data obtained in the six independent test units for the VWF:Ag concentration and the SNA binding of these samples.

TABLE 3

VWF: Ag and SNA binding of spiked samples

| | CHO cell-derived rVWF spiked to human plasma | | | | | | | | |
|---|---|---|---|---|---|---|---|---|---|
| | 0 | 0.2 U | 0.4 U | 0.5 U | 0.6 U | 0.8 U | 1.0 U | 1.2 U | 1.5 |
| VWF: Ag | | | | | | | | | |
| Test 1 | 0.85 | 1.10 | 1.27 | 1.35 | 1.39 | 1.70 | 1.90 | 2.00 | 2.20 |
| Test 2 | 1.09 | 1.10 | 1.24 | 1.32 | 1.47 | 1.94 | 2.24 | — | — |
| Test 3 | 0.95 | 1.06 | 1.22 | 1.34 | 1.39 | 1.80 | 1.89 | 2.06 | 2.15 |
| Test 4 | 0.95 | 1.09 | 1.20 | 1.38 | 1.43 | 1.62 | 1.89 | 2.00 | 2.07 |
| Test 5 | 0.95 | 1.13 | 1.22 | 1.42 | 1.49 | 1.68 | 1.85 | 1.95 | 2.09 |
| Test 6 | 0.96 | 1.16 | 1.40 | 1.38 | 1.48 | 1.62 | 1.81 | 2.04 | 2.13 |
| Mean | 0.96 | 1.11 | 1.26 | 1.37 | 1.44 | 1.73 | 1.93 | 2.01 | 2.13 |
| RSD | 8.0 | 3.1 | 5.8 | 2.6 | 3.1 | 7.2 | 8.1 | 2.1 | 2.4 |
| SNA | | | | | | | | | |
| Test 1 | 134.6 | 94.3 | 80.2 | 76.4 | 71.5 | 62.9 | 60.8 | 55.0 | 56.3 |
| Test 2 | 110.0 | 90.0 | 81.6 | 73.7 | 74.8 | n.d. | n.d. | 43.0 | 42.6 |
| Test 3 | 135.1 | 92.7 | 85.7 | 77.5 | 73.4 | 59.8 | 55.6 | 56.4 | 56.0 |
| Test 4 | 117.1 | 90.3 | 87.8 | 85.2 | 76.7 | 58.8 | n.d. | 56.0 | 50.6 |
| Test 5 | 113.8 | 90.7 | 82.0 | 76.1 | 71.9 | 60.6 | 53.1 | 50.6 | 46.6 |
| Test 6 | 130.6 | 96.0 | 83.4 | 85.0 | 91.9 | 70.8 | 67.6 | 54.5 | 53.2 |
| Mean | 123.5 | 92.3 | 83.5 | 78.9 | 76.6 | 62.6 | 59.3 | 52.6 | 50.9 |
| RSD | 9.1 | 2.6 | 3.4 | 6.2 | 9.6 | 7.7 | 10.8 | 9.8 | 10.7 |

Plasma VWF at a concentration of 0.96 U had a mean SNA binding corresponding to 123.5% of that measured for a reference plasma pool. Using this mean SNA binding measured for the human plasma sample containing no CHO-cell derived rVWF, the hypothetical SNA binding was calculated for the spiked samples under the assumption that the VWF:Ag measured was only plasma VWF. These data are shown in Table 4.

TABLE 4

Calculation of the hypothetical SNA binding for the plasma samples spiked with CHO cell-derived rVWF

| | CHO cell-derived rVWF spiked to human plasma | | | | | | | | |
|---|---|---|---|---|---|---|---|---|---|
| | 0 | 0.2 | 0.4 | 0.5 | 0.6 | 0.8 | 1 | 1.2 | 1.5 |
| Total VWF | 0.96 | 1.11 | 1.26 | 1.37 | 1.44 | 1.73 | 1.93 | 2.01 | 2.13 |
| rVWF | | 0.15 | 0.30 | 0.41 | 0.48 | 0.77 | 0.97 | 1.05 | 1.17 |
| SNA binding expected | 123.5 | 142.6 | 162.2 | 175.9 | 185.8 | 222.5 | 248.7 | 259.0 | 274.2 |
| SNA binding found | 123.5 | 92.3 | 83.5 | 79.0 | 76.6 | 62.6 | 59.3 | 52.6 | 50.9 |
| Difference | 0.0 | 50.3 | 78.7 | 96.9 | 109.2 | 159.9 | 189.4 | 206.4 | 223.4 |
| SD | n.d. | 1.3 | 2.7 | 6.0 | 10.5 | 12.4 | 20.5 | 20.1 | 23.9 |

Figure 2:
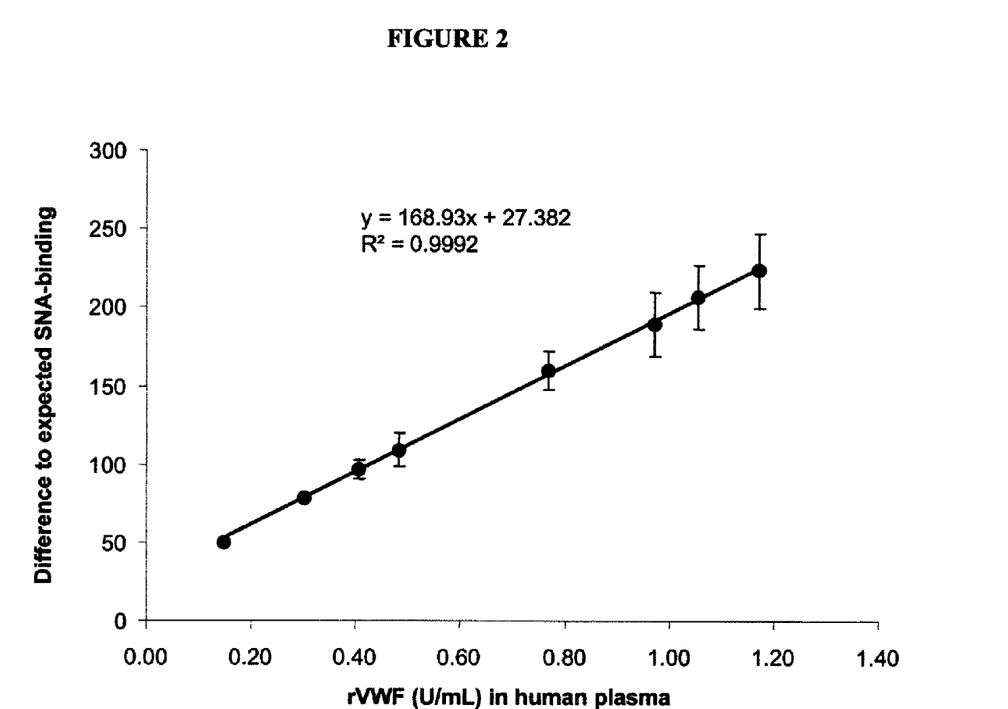
FIG. 2 is a plot of an eight-point calibration curve correlating the difference in expected and observed SNA binding in a sample with the amount of recombinant protein

Similar to the 4-point calibration assay described above, the difference to the expected SNA binding correlated well with the concentrations of CHO cell-derived rVWF spiked to human plasma even when 8 concentrations in a narrower spiking range where investigated. A plot of the 8-point calibration curve correlating the difference in SNA binding with the amount of recombinant protein is shown in FIG. 2.

These results show that the amount of recombinant protein in a sample of human plasma can readily be differentiated from naturally-produced protein in the sample, based on the differential expression of carbohydrate moieties. This type of assay is useful in the clinical setting to determine the amount of exogenous/therapeutic protein being administered and its penetration into the blood stream compared to the amount of naturally-produced protein. This assay is also useful to compare the efficacy of one therapeutic to another by comparing serum half-life in vivo.

Numerous modifications and variations in the invention as set forth in the above illustrative examples are expected to occur to those skilled in the art. Consequently only such limitations as appear in the appended claims should be placed on the invention.

What is claimed:

1. A method to quantitate the amount of recombinant protein (rP) in a sample containing both plasma-derived protein (pdP) and recombinant protein (rP) from an individual, wherein the plasma-derived protein and recombinant protein are the same protein having different glycosylation patterns, said different glycosylation patterns giving rise to different degrees of binding to lectin, wherein the combined amount of plasma-derived protein and recombinant protein is equal to total protein (pdP+rP=tP), said total protein being pre-determined, said method comprising the steps of:
  (a) contacting the sample from the individual with a lectin composition and detecting differential protein binding of the plasma-derived protein and recombinant protein to the lectin composition,
  (b) calculating a difference between lectin binding to the total protein in said sample from said individual and expected lectin binding to a total protein in a reference sample of equal volume having an amount of the plasma-derived protein equal to the total protein (tP) in the sample from the individual, wherein the difference in lectin binding correlates to the amount of recombinant protein in the sample from the individual.

2. The method of claim 1 wherein the lectin is labeled with a detectable label.

3. The method of claim 2 wherein the label is biotin.

4. The method of claim 1 wherein the lectin is *Sambucus Nigra agglutinin* (SNA).

5. The method of claim 1 wherein the sample is serum.

6. The method of claim 1 wherein the protein is a blood clotting factor.

7. The method of claim 1 wherein the blood clotting factor is selected from the group consisting of von Willebrand factor (vWF), Factor VIII (FVIII), Factor VII (FVII), and Factor IX (FIX).

8. The method of claim 1 wherein the recombinant protein is produced by Chinese hamster ovary (CHO) cells.

9. The method of claim 1 wherein the recombinant protein is produced in insect cells.

10. The method of claim 1 wherein the plasma-derived protein comprises ÿ,6-neuraminic acid and the recombinant protein lacks α,2,6-neuraminic acid.

11. The method of claim 1 wherein the sample is contacted with a binding agent specific for the protein prior to contacting with the lectin composition.

12. The method of claim 11 wherein the protein binding agent is bound on a solid support.

13. The method of claim 11 wherein the protein binding agent is in solution.

14. The method of claim 11 wherein the protein binding agent is an antibody.

15. The method of claim 14 wherein the antibody is a monoclonal antibody.

16. The method of claim 1 further comprising, after contacting with the binding agent, contacting the sample with a periodate solution.

17. The method of claim 1 wherein the recombinant protein is a fragment, variant or analog of the plasma-derived protein.

* * * * *